| United States Patent [19] | [11] Patent Number: 4,769,027 |
| Baker et al. | [45] Date of Patent: Sep. 6, 1988 |

[54] DELIVERY SYSTEM

[75] Inventors: Richard W. Baker, Mountain View, Calif.; Kelly L. Smith, Bend; James W. Brooke, Sisters, both of Oreg.

[73] Assignee: Burroughs Wellcome Co., Research Triangle Park, N.C.

[21] Appl. No.: 16,966

[22] Filed: Feb. 24, 1987

Related U.S. Application Data

[63] Continuation of Ser. No. 641,058, Aug. 15, 1984, abandoned.

[51] Int. Cl.$^4$ .............................................. A61M 31/00
[52] U.S. Cl. ..................................... 424/493; 424/473
[58] Field of Search ............... 604/890, 892, 893, 894, 604/896; 424/14, 16, 21–22, 28

[56] References Cited

U.S. PATENT DOCUMENTS

| 2,099,402 | 1/1934 | Keller | 424/21 |
| 3,577,512 | 5/1971 | Shepherd et al. | 424/21 |
| 3,845,770 | 11/1974 | Theeuwes et al. | 604/893 |
| 4,455,143 | 6/1984 | Theeuwes et al. | 604/890 |
| 4,576,604 | 3/1986 | Guittard et al. | 604/890 |
| 4,586,922 | 5/1986 | Theeuwes et al. | 604/56 |

FOREIGN PATENT DOCUMENTS 280478  4/1970  Australia .
1326995 8/1973  United Kingdom .

Primary Examiner—C. Fred Rosenbaum
Assistant Examiner—Gene B. Kartchner
Attorney, Agent, or Firm—Donald Brown

[57] ABSTRACT

Prills of pharmaceutically acceptable material are coated first with a water-permeable polymeric matrix containing a water-soluble pharmaceutically beneficial agent and then overcoated with a water-permeable film containing dispersed therein a water-soluble, particulate pore-forming material.

4 Claims, 1 Drawing Sheet

DELIVERY SYSTEM

This application is a continuation of application Ser. No. 641,058 filed Aug. 15, 1984 now abandoned.

FIELD OF THE INVENTION

This invention relates to a device which provides the controlled, continuous dispensing of a water-soluble beneficial agent for a predetermined period of time. Moreover, the invention relates to such a device powered by an osmotic pumping mechanism, to the preparation of such a device and to the use of such a device in the medical, veterinary and other fields.

BACKGROUND OF THE INVENTION

Systems for the delivery of pharmaceutically beneficial agents are well known in the art. Dispensing systems which deliver their contents by diffusion through a permeable polymer coating or wall are well known but suffer from severe limitations. For example, many pharmaceutically beneficial agents cannot be delivered from such diffusion controlled devices. In many instances permeation rates through the permeable polymer coating are inadequate to provide useful concentrations of the beneficial agent. In many others, the beneficial agent has such a high molecular weight that it will not diffuse through the polymer coating.

Also well known are delivery systems which operate by means of an osmotic pumping mechanism. In a typical delivery system of this type the beneficial agent is contained within a continuous, semi-permeable film, e.g. a capsule or a film coating, having a hole of predetermined size drilled therethrough. In operation the delivery system is placed in the appropriate aqueous environment, e.g. the stomach or cul-de-sac of the eye, whereupon it imbibes water through the semi-permeable film, thereby dissolving at least in part the contents of the delivery system. This causes an increase in the internal (osmotic) pressure, which results in the dissolved contents being continuously pumped out of the delivery system through the hole at a controlled rate over a predetermined period of time.

The devices taught in the art have a number of deficiencies. They are, in most cases, complex devices having multiple parts or requiring special fabrication steps. For example, many require the drilling of a hole through the film coating of each device. Consequently, the delivery system itself is relatively inexpensive to fabricate and contributes substantially to the final cost of the product.

Prior art devices each having a single passageway through which their dissolved contents are delivered have other disadvantages. When the beneficial agent contained and delivered by such a device is irritating to the biological tissue in the region in which the device is used, local tissue irritation could be a problem at the locus of delivery of the agent, i.e. in the vicinity of the hole through which the concentrated agent is pumped. Also, the drilling of individual holes and other means of forming single passageways are not amenable to the preparation of osmotically driven prills.

Alternatives to drilling individual holes through the semi-permeable film have been disclosed. For example, the use of a friable, inexpandable wall has been described which fractures when it imbibes water to provide cracks and fissures through which the contents are then delivered. Passageways provided by erosion of bioerodible fibers incorporated in the wall of the delivery device have also been described.

There is a very large body of art describing the various delivery systems. The U.S. patents below are cited as representative of the controlled delivery system art: U.S. Pat. Nos. 3,845,770; 3,916,899; 4,016,880; 4,160,452; and 4,200,098.

SUMMARY OF THE INVENTION

The present invention provides a method and means for dispensing in a controlled, continuous manner therapeutically effective amounts of water-soluble drugs for a predetermined period of time to achieve a predetermined useful effect in animals, especially mammals, including in particular human beings.

In one aspect, sugar/starch prills (or prills of other pharmaceutically acceptable materials such as salts, waxes, and the like) are coated with a polymeric matrix containing the beneficial agent and then overcoated with a water-permeable film containing a water-soluble, particulate pore-forming material. The matrix material may be the same polymeric material as that used for the overcoat, but it is preferably a polymeric material having a higher permeability to water than that of the overcoat polymer. In the case where the beneficial agent is sufficiently water-soluble, the prill core may be of a non-water-soluble material. In the case where the beneficial agent has a low water solubility, the prill core should be water-soluble and act to increase the osmotic pressure.

Such osmotic prills have several key advantages over prior-art tablets. First, an equivalent dosage in prill form has a much larger total membrane surface area than does a tablet, and can therefore exhibit much higher release rates. This is especially important for beneficial agents with low water solubilities. Second, agents with widely different water solubilities and dosage requirements can be combined in a single dose by mixing, in the proper ratio, prills containing the single agents. Such combination doses are difficult if not impossible to achieve in tablet form. Prills may also be combined with unencapsulated beneficial agent in the same capsule to provide immediate delivery of the agent as well as controlled release of additional amounts of the agent. Finally, in the case of orally administered pharmaceuticals, patient acceptance of doses in capsule form (containing prills) is often greater than their acceptance of doses in tablet form.

In another aspect of the present invention there is provided a method of simply and reproducibly mass producing osmotically driven, controlled release devices for dispensing water-soluble beneficial agents.

As used herein prills are pellets, the longest dimension of which is about 0.1 to about 4.0 mm, preferably about 0.3 to about 2.0 mm. Prills are preferably substantially spherical, but they may be ovoidal or even of irregular shape. Prills may consist of pharmaceutically acceptable excipients such as sugars, e.g. sucrose, mannitol and the like; salts, e.g. sodium chloride; starch; waxes and the like. They may consist of the beneficial agent, either alone or in combination with an excipient or a polymeric matrix.

It is contemplated that the controlled release device of the present invention also has utility in non-animal environments such as in agriculture (e.g., for the controlled delivery of fertilizers, soil trace minerals or elements, fungicides, herbicides and the like) or other environments in which it would come into contact with water from time to time or continuously.

When the device of the present invention is used, e.g., by oral administration to a human being, it comes into contact with an aqueous environment. Water is imbibed through the semi-permeable film coating, in the process leaching out the water-soluble particles in the film coating. The imbibed water dissolves the water-soluble beneficial agent as well as osmotic enhancing agents present. This sets up the osmotic gradient which actively brings in water through the semi-permeable membrane thereby increasing the pressure inside the devide, resulting in the saturated (or partially saturated) solution of the beneficial agent being pumped out through the micro-passageways created by the water dissolving the pore-forming, water-soluble particles imbedded in the film coating of the device.

BRIEF DESCRIPTION OF THE DRAWINGS

The drawings are not drawn to scale. They are set forth to illustrate the invention, and are as follows.

In the drawings and specifications, like parts are identified by like numbers.

DETAILED DESCRIPTION OF THE DRAWINGS

Figure 1:
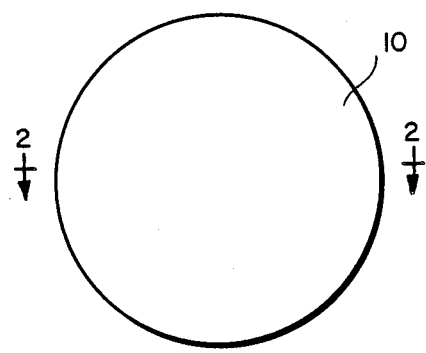
FIG. 1 is a view of a controlled release prill for the delivery of a beneficial agent.

The drawings illustrated here are intended to schematically represent the controlled delivery device of the invention and are not to be considered limiting. FIG. 1 represents one example of the delivery device, indicated by the numeral 10, a prill for oral administration to an animal.

Figure 2A:
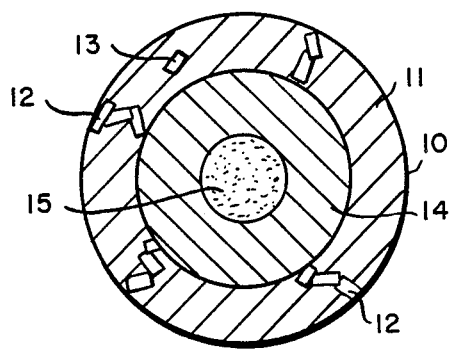
FIG. 2(a) is a sectional view taken along line 2—2 schematically illustrating the functional structure of the prill as manufactured, i.e. before use.
Figure 2B:
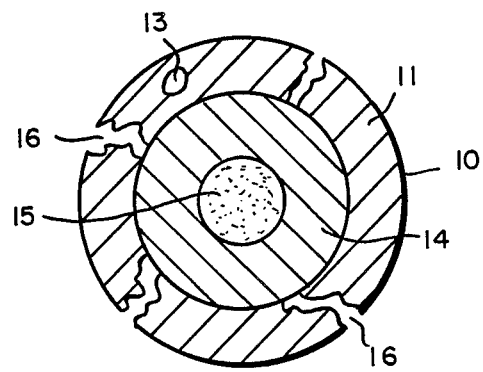
FIG. 2(b) is the same sectional view as depicted in FIG. 2(a) schematically illustrating the functional structure of the prill after the pore-forming material has been dissolved out during use.

In FIG. 2(a) the prill 10 of FIG. 1 is depicted in cross-section illustrating the structure of the prill as manufactured. Prill 10 comprises a water-permeable, water-insoluble film coating 11 which may contain in the film coating plasticizers and/or water-permeability-modifying agents and which has dispersed therein particulate, pore-forming material 12 and 13. The individual particles of pore-forming material 12 are in substantial contact with one another across the thickness of film 11 and, when the prill 10 is used for its intended use, are dissolved out to form the pores 16 therethrough as shown in FIG. 2(b). The individual particles of pore-forming material 13 are not in contact with one another across the thickness of film 11 and, when the prill 10 is used for its intended use, do not form pores through film 11. The film coating 11 encompasses a layer 14 which comprises a polymeric matrix containing at least one water-soluble beneficial agent. Layer 14 encompasses the core 15 which comprises an excipient which may be water-soluble or water-insoluble. Core 15 may also comprise the beneficial agent either alone or in combination with an excipient or a polymeric matrix.

FIG. 2(b) depicts the same cross-section as shown in FIG. 2(a) after sufficient exposure to its environment of use to dissolve the pore-former particles.

DETAILED DESCRIPTION OF THE INVENTION

The novel controlled delivery device of the present invention is simple in construction, permitting efficient mass production by conventional techniques. It is simple in operation, being no more complex to use than a conventional tablet or capsule.

Water-insoluble, water-permeable polymers suitable for forming the film coating of the device of the present invention include homopolymers and copolymers which are semipermeable. By semi-permeable is herein meant permeable to solvent but not to solute, i.e., permeable to water but not permeable to the beneficial agent or osmotic enhancing agent dissolved therein. Suitable polymeric materials include cellulose esters such as mono-, di- and triacylates including mixed esters, cellulose ethers such as ethyl cellulose, poly(dialkylsiloxanes), poly(methacrylic acid) esters, poly(acrylic acid) esters, poly(phenylene oxides), poly(vinyl alcohols), aromatic nitrogen-containing polymers, regenerated cellulose and other membrane-forming materials suitable for use in reverse osmosis or dialysis application. Some examples of such suitable film-forming materials include cellulose acetate, cellulose diacetate, cellulose triacetate, cellulose propionate, cellulose acetate butyrate, cellulose acetate propionate, cellulose tripropionate, ethyl cellulose and the like. The film coating, in addition to being semipermeable, must not adversely affect the beneficial agent or the animal receiving the device. The thickness of the film coating is desirably 10 to 500 $\mu$m, preferably 25 to 250 $\mu$m.

Plasticizers may be used in the semipermeable polymeric film coating of the present invention. Typical plasticizers which may be used include esters such as the phthalates, phosphates, citrates, adipates, tartrates, sebacates, succinates, glycolates, glycerolates, benzoates and myristates, sulfonamides and the like. Specific examples include dimethyl phthalate, dipropyl phthalate, di-(2-ethylhexyl) phthalate, tributyl phosphate, triacetyl phosphate, and tributyl citrate. The plasticizer must be compatible with the other materials of the film coating. It should also have a high degree of permanence, i.e., it should remain in the polymeric film and not migrate to the surface to an appreciable extent. It should also have no adverse effect on the beneficial agent or the animal receiving the device.

The term "water-permeability-modifying agent" as used herein means a compound or material which when added to the semi-permeable film-forming material modifies the water permeability of the film produced therefrom, enhancing or increasing its permeability to water. Permeability-modifying agents include the poly(alkylene glycols), esters and polyesters of poly(alkylene glycols), polyhydric alcohols and esters and polyesters of polyhydric alcohols. Specific examples of suitable water-permeability-modifying agents include poly(ethylene glycols) 300, 400, 600, 1500 and 1540, poly(propylene glycol), 1,3-butyleneglycol, glycerine, ethylene glycol dipropionate, ethylene glycol butyrate and the like.

The pore-forming material must be particulate in nature, with a maximum particle size preferably not exceeding about 500 $\mu$m in its longest dimension and an average particle size from about 1 $\mu$m to about 300 $\mu$m, more preferably having an average particle size from about 5 $\mu$m to about 100 $\mu$m. It must be soluble in water or aqueous media and insoluble in the organic solvent in which the polymeric film-forming material is dissolved during the film-coating process. Suitable pore-forming materials include the water-soluble sugars, e.g., lactose, sucrose, sorbitol and mannitol, and water-soluble, salts, e.g., sodium carbonate, sodium chloride, calcium chloride, potassium chloride and sodium sulfate, and the like. When the device of this invention is intended for pharmaceutical use, the pore-forming material must be pharmaceutically acceptable. A portion of the beneficial agent may be used as the pore-forming material, and in certain formulations this may be preferred.

Osmotic enhancing agents are water-soluble materials having a high molar water solubility (high water solubility on a molar basis) which are capable of achieving in solution an osmotic pressure greater than that of the aqueous environment of the device of this invention when in use. Suitable osmotic enhancing agents include sugars, e.g. sucrose, lactose, fructose, mannitol and the like; salts, e.g. sodium chloride, potassium chloride, sodium carbonate and the like; as well as other water-soluble organic or inorganic compounds. When used in devices for human or veterinary use the osmotic enhancing agents should be pharmaceutically acceptable.

The delivery devices of the present invention are manufactured by standard techniques. In one embodiment prills, e.g., sucrose prills, are coated in a fluidized-bed coater with a solution of a film-forming polymer containing a large proportion of beneficial agent, about 0.5 to about 5.0 times as much as the polymer by weight. The solution (or suspension if the beneficial agent is not soluble in the polymer solvent) is sprayed into the suspending air stream, thereby coating the prills with beneficial-agent-loaded, water-permeable polymer film. After the prills are coated to the desired beneficial-agent content, the coated prills are dried and then overcoated with a controlled-porosity, water-permeable membrane by spraying into the suspending air stream of the fluidizedbed coater a solution of the film-forming polymer, plasticizer (if desired) and permeability-modifying agent (if desired) containing the pore-forming material suspended therein until the prills have the desired film thickness. They are then dried.

Beneficial agents suitable for use in the devices of this invention must be water soluble and produce a beneficial effect when delivered from the device. Such beneficial agents include pharmaceutical agents for use in human and veterinary medicine, nutrients, pesticides, insecticides, fungicides, herbicides, algicides, vitamins, fertilizers, soil trace minerals or elements and the like. Specific examples include d-pseudoephedrine hydrochloride; bupropion hydrochloride; soluble potassium salts such as potassium chloride, potassium citrate, potassium gluconate, and the like; chlorpheniramine maleate; propranolol hydrochloride; cimetidine; phenylpropanolamine hydrochloride; dextromethorphan hydrobromide; ascorbic acid; aspirin; acetaminophen, codeine salts; methomyl; copper sulfate; ammonium nitrate and the like.

When used in human or veterinary medicine the devices of this invention may be administered in any appropriate manner. For example, administration by oral (capsule), subcutaneous implantation, inter alia may be employed with these devices.

The following examples further illustrate but should not be construed as limiting the invention.

EXAMPLE 1

A total of 40 g of sugar/starch see prills (Nu-Pareil TM 20/25 mesh prills from Ingredient Technology Corp., Pennsauken, N.J.) was placed in cylindrical bed (16 in. long×1.5 in. diameter) and fluidized with dry compressed air at 30 psi. The prills were then coated with a solution of 12 g of cellulose acetate (CA 398-10 from Eastman Chemical Products, Inc., Kingsport, Tenn.) and d-pseudoephedrine hydrochloride (36 g) in ethanol (200 ml) and dichloromethane (400 ml) using an air brush at 30 psi. Agglomeration was avoided by intermittent application with partial drying. The prills were removed from the bed and allowed to dry for two hours. They were then returned to the fluidized bed and coated with a solution of 7 g of cellulose acetate (CA 398-10) and 1 g of poly(ethylene glycol) (Polyglycol E-400 from Dow Chemical Co., Midland, Mich.) in 240 ml of acetone containing 2 g of powdered sodium carbonate (particle size: 30–200 $\mu$m) is suspension. The osmotically driven, controlled release prills thus formed were then allowed to dry.

Drug release rates were determined for the prills by placing them in sodium chloride solutions of different concentrations at 37° C. to vary the osmotic pressure driving force for drug release, and periodically measuring the d-pseudoephedrine hydrochloride concentration. When the sodium chloride concentration was 0%, the drug release rate was 90 mg/hr; when it was 5%, the release rate was 75 mg/hr; when it was 10%, the release rate was 45 mg/hr; and when it was 20%, the release rate was 10 mg/hr.

EXAMPLE 2

Sucrose seed prills (Nu-Pareil TM) were coated with an aspirin (75%)-CA-398-10 (25%) mixture essentially following the procedure of Example 4 but using acetone (containing 10% by weight of total solids) instead of ethanol-dichloromethane. The coated prills were dried and then overcoated with a 40:40:20 mixture of cellulose acetate (CA-398-40 from Eastman Chemical Products, Inc., Kingsport, Tenn.): Polyglycol E-400: impalpable lactose (particle size: 5–20 $\mu$m) in acetone (5% by weight total solids). The osmotically driven, controlled release prills thus formed were then allowed to dry.

Drug release rates were determined as in Example 3. After 2 hr. about 60% of the aspirin had been released; after 4 hr. about 80% had been released; and after 8 hr. about 90% had been released.

It will be appreciated from the foregoing that what we will claim may comprise any novel feature described herein, principally, but not exclusively, for example:

(a) A delivery system for the controlled release of a water-soluble beneficial agent comprising (i) a water-insoluble, water permeable film containing discrete, water-soluble particles which during use dissolve in the aqueous environment thereof to leave pores in said film, and (optionally) containing a water-permeability-enhancing amount of a water-permeability-modifying agent and a plasticizer, said film encompassing (ii) a layer comprising a polymeric matrix containing at least one water-soluble beneficial agent, said layer encompassing (iii) a core.

(b) A delivery system according to (a) above wherein said core comprises a water-soluble excipient.

(c) A delivery system according to (a) above wherein said core comprises a water-insoluble excipient.

(d) A delivery system according to (a) above wherein said core comprises at least one water-soluble beneficial agent.

(e) A method of preparing a device as defined in (a) above substantially as hereinbefore described.

(f) A method of delivering a water-soluble beneficial agent in a controlled, continuous manner using a device as defined in (a) above.

What we claim is:

1. A pellet having a longest dimension of 0.1 to 4.0 mm, said pellet comprising a core, a first film of a polymer which is water-permeable containing a beneficial agent, said first film overcoating said core, the weight of said beneficial agent being about 0.5 to about 5.0 times the weight of the polymer of said first film, and a second film overlying said first film, said second film containing a polymer which is water-permeable containing water-soluble particlate pore-forming material, the size of the water-soluble particles being less than the thickness of the film.

2. The pellet of claim 1 in which the first film polymer has a higher permeability to water than the polymer of said second film.

3. The pellet of claim 1 in which the core is water-soluble.

4. The pellet of claim 1 in which the core is water-soluble.

* * * * *